(12) United States Patent
Yang et al.

(10) Patent No.: US 8,263,048 B2
(45) Date of Patent: Sep. 11, 2012

(54) CALCIUM PHOSPHATE COMPLEX FOR ORAL CARE APPLICATIONS, ITS PREPARATION METHOD, AND COMPOSITIONS CONTAINING THE SAME

(75) Inventors: Jen-Chang Yang, Taipei (TW); Sheng-Yang Lee, Taipei (TW); Der-Zen Liu, Taipei (TW); Nai-Chia Teng, Taipei (TW); En-Sheng Ke, Taipei (TW); Chien Chung Chen, Taipei (TW); Dian-Yu Ji, Taipei (TW); Chen-Feng Ma, Taipei (TW); Hong-Da Wu, Taipei (TW)

(73) Assignee: Taipei Medical University, Taipei (TW)

( * ) Notice: Subject to any disclaimer, the term of this patent is extended or adjusted under 35 U.S.C. 154(b) by 0 days.

(21) Appl. No.: 12/975,052

(22) Filed: Dec. 21, 2010

(65) Prior Publication Data

US 2011/0150791 A1   Jun. 23, 2011

(30) Foreign Application Priority Data

Dec. 22, 2009   (TW) .............................. 98144259 A (51) Int. Cl.
*A61K 8/55* (2006.01)
*A61Q 11/00* (2006.01)

(52) U.S. Cl. ........... 424/57; 514/1.1; 424/401; 424/602; 433/217.1

(58) Field of Classification Search .................. 424/52; 426/74

See application file for complete search history.

(56) References Cited

U.S. PATENT DOCUMENTS

| | | | |
|---|---|---|---|
| 5,447,732 A * | 9/1995 | Tanimoto et al. ............... 426/74 |
| 5,837,674 A | 11/1998 | Kumagai et al. |
| 6,306,822 B1 | 10/2001 | Kumagai et al. |
| 6,863,882 B2 | 3/2005 | Dixon, Jr. et al. |
| 7,455,854 B2 | 11/2008 | Gower et al. |
| 2003/0124066 A1 | 7/2003 | Dixon, Jr. et al. |
| 2003/0152525 A1 | 8/2003 | Dixon, Jr. et al. |
| 2003/0232071 A1 | 12/2003 | Gower et al. |
| 2004/0131562 A1 | 7/2004 | Gower et al. |
| 2005/0152990 A1 | 7/2005 | Gower et al. |
| 2005/0175959 A1 | 8/2005 | Ahron et al. |
| 2006/0204580 A1 | 9/2006 | Gower et al. |
| 2006/0204581 A1 | 9/2006 | Gower et al. |
| 2008/0171001 A1 | 7/2008 | Engelman et al. |
| 2009/0035355 A1 | 2/2009 | Hausmanns et al. |
| 2009/0042161 A1 | 2/2009 | Ahron et al. |

FOREIGN PATENT DOCUMENTS

| | | |
|---|---|---|
| TW | 200600111 | 1/2006 |
| TW | 200600112 | 1/2006 |
| TW | 200610544 | 4/2006 |
| TW | 200637605 | 11/2006 |
| TW | 200640531 | 12/2006 |
| TW | 200735895 | 10/2007 |
| TW | 200738272 | 10/2007 |
| TW | 200806335 | 2/2008 |

* cited by examiner

*Primary Examiner* — Walter Webb (74) *Attorney, Agent, or Firm* — McDonnell Boehnen Hulbert & Berghoff LLP (57) ABSTRACT

The invention is directed to a calcium phosphate complex and the composition containing the same for oral care applications, in which the calcium phosphate complex is formed by chelating the γ-polyglutamic acid (γ-PGA) with amorphous calcium phosphate (ACP). This complex can prevent crystallization of ACP and maintain its high solubility. The calcium phosphate complex has superior mucoadhesion properties, allowing it to remain in the mouth longer and offering effective buffering, by which dental caries can be alleviated and prevented.

22 Claims, 6 Drawing Sheets

CALCIUM PHOSPHATE COMPLEX FOR ORAL CARE APPLICATIONS, ITS PREPARATION METHOD, AND COMPOSITIONS CONTAINING THE SAME

FIELD OF THE INVENTION

This invention relates to a calcium phosphate complex for oral care, which enables prevention and alleviation of dental caries, its preparation and compositions containing the same.

BACKGROUND OF THE INVENTION

Teeth are mainly composed of enamel, dentin, and pulp chamber rich with nerves and blood vessels. Enamel and dentin are highly calcified hard tissue because of the component, hydroxyapatite (HAp). However, if they are stayed in an acidic environment for a period of time, they will lose mineral and become soft by the erosion of acid. After a prolonged time, the etching will decay teeth and dental caries will occur. Dental caries is a multifactor disease and concerns oral health.

Teeth may be damaged by acidic metabolites etching the dental surface, which causes loss of mineral substance and formation of caves on the enamel, and penetrating into the dentin or further into the pulp chamber. Acidic metabolites can be produced by food residue (such as carbohydrate) in the mouth. In addition, the decrease of saliva with age, the side effects of medication (such as anti-depression drug), or the deterioration of physical conditions will also reduce the oral buffering capacity, resulting in the decrease of the pH level and the formation of an acidic oral environment. As a result, the chance to get dental caries is largely increased.

In the oral environment, the phosphates and calcium ions in the liquid phase (saliva) and the solid phase (enamel) maintain a dynamic equilibrium between demineralization and remineralization. The equilibrium may be imbalanced by various factors, which leads to an increase of demineralization. Therefore, teeth can be repaired and caries can be prevented or alleviated so as to avoid pain or tooth loss by inhibiting the oral bacterial growth or buffer the acidity caused by soft drinks or bacteria metabolism.

Various product additives such as xylitol and fluoride were known in the prior art to diminish caries. Xylitol can inhibit bacteria growth, thereby decreasing oral acidity, and fluoride can increase anti-acidity of teeth. Although the above-mentioned additives can decelerate demineralization so as to prevent caries, these components cannot strengthen teeth directly. In addition, fluoride cannot sustain in oral for long time and can be lost due to saliva flow, thus limiting the benefit.

According to the dynamic equilibrium mechanism, remineralization can be improved by the increase of the concentration of phosphate ions and calcium ions in the oral environment. Among various calcium phosphate salts, amorphous calcium phosphate (ACP) is considered as an ideal source of calcium ions and phosphate ions because of its advantageous solubility. However, the solubility of ACP decreases after contacting water in a physiological environment as it transforms into crystalline hydroxyapatite ($Ca_{10}(PO_4)_6(OH)_2$). Furthermore, ACP only remains in mouth or dental surface for a short period, so its effect is difficult to be fully released. In 2004, Eric Reynolds of the University of Melbourne, Australia, used peptide fragments produced from enzyme-cleaved casein as carriers to chelate with ACP to form casein phosphopeptide-amorphous calcium phosphate complex (CPP-ACP) and constitute a core-shell structure to stabilize the amorphous structure of ACP and prevent ACP from transforming into crystalline calcium phosphate. The complex maintains solubility of ACP, attaches ACP to oral surfaces in a more secure way, keeps ACP for a longer time and extends its efficacy in preventing caries. Although CPP-ACP is effective in preventing caries, its popularity is limited because of the milk protein allergy among subjects, which is triggered by casein.

Therefore, the prior art on oral compositions attempting to solve the above-mentioned problems is extensive.

Taiwan Patent Publication No. 200600111 discloses a dental whitening method, comprising separately applying a whitening composition to the dental surface, wherein the whitening composition comprises at least one of oral acceptable peroxide, and introducing a micronized active composition in a volume of at most 2.5 ml to the surface. The reference discloses that the steps of applying the whitening composition and introducing the active composition are performed separately. In addition, the application mentions γ-polyglutamic acid as one of the options for controlling calculus, calcium glycerol phosphate as one of the options for controlling dental plaque, and calcium phosphate as one of the abrasives. It does not, however, mention the combination of γ-PGA and calcium phosphate and the effects that it may produce.

Taiwan Patent Publication No. 200600112 discloses a kit used in oral care, comprising (a) a composition, including an oral treatment agent, and (b) an absorption fabric which is soaked in or coated by an oral acceptable pre-modifier, wherein the oral treatment agent is an oral acceptable peroxide and the pre-modifier is an alkalizing agent or active agent of an oral care agent. The application also mentions γ-polyglutamic acid as one of the options for controlling calculus, calcium glycerol phosphate as one of the options for controlling dental plaque, and calcium phosphate as one of the abrasives. Nevertheless, it does not mention the combination of γ-PGA and calcium phosphate and the effects that it may produce.

Taiwan Patent Publication No. 200610544 discloses a composition for application to the tooth surface for delivering the oral treatment material. The composition is a flexible thin film, comprising an oral treatment material distributed in an effective amount and polymeric matrix film. The matrix has weight selected hydrophobic parts and hydrophilic parts to make the film substantially dissolvable in the saliva during oral treatment. The application also mentions γ-polyglutamic acid as one of the options for controlling calculus, and calcium glycerol phosphate as one of the options for controlling dental plaque. Nevertheless, it does not mention the combination of γ-PGA and calcium phosphate and the effects that it may produce.

Taiwan Patent Publication No. 200637605 discloses a toothpaste composition comprising a wetting agent, an abrasive, and an antibacterial component including ursolic acid and carnosic acid. The application also mentions γ-polyglutamic acid as one of the options for controlling calculus, and calcium phosphate as one of the options for controlling dental plaque. Nevertheless, it does not mention the combination of γ-PGA and calcium phosphate and the effects that it may produce.

Taiwan Patent Publication No. 200640531 discloses an oral care composition comprising one or more oregano extract active components in a safe and effective amount, and an oral acceptable carrier. The application also mentions γ-polyglutamic acid as one of the anti-calculus agents, and calcium glycerol phosphate as one of the anti-dental plaque agents. Nevertheless, it does not mention the combination of γ-PGA and calcium phosphate and the effects that it may produce.

Taiwan Patent Publication No. 200735895 discloses a particle comprising a core comprising oxide or its salt and a bio-adhered polymer, wherein the bio-adhered polymer is attached to the oxide or its salt. The application mentions that the bio-adhered polymer can be peptide and the oxide can be alkaline earth metal phosphate salt. Nevertheless, the focus is on the ability of the particle and the bio-adhered polymer to prevent bacteria from adhering or attaching to the fixing part. The application does not mention the combination of γ-PGA and calcium phosphate, let alone that such combination can decrease oral acidity, enhance adhesion of calcium ions to oral surfaces, and improve dental caries.

Taiwan Patent Publication No. 200738272 discloses a dental composition comprising an active dental material, at least one effective sweetener, and at least one sweet modifier. It can comprise an additional sweet modifier and an inorganic phosphate salt. Nevertheless, it does not mention the combination of γ-PGA and calcium phosphate and the effects that it may produce.

Taiwan Patent Publication No. 200806335 discloses a diphase whitening oral care composition comprising: (a) a first phase including a whitening agent that is substantially free of water and oral acceptable carrier, and (b) a second phase including an anti-calculus agent and abrasive, wherein the first phase and the second phase are separately placed before formulation. The application mentions calcium phosphate as one of the abrasives or polishing agents, and γ-PGA as one of the anti-calculus agents. Nevertheless, it does not mention the combination of γ-PGA and calcium phosphate and the effects that it may produce.

US 20050175959 provides a system for delivery of materials to the dental surfaces of an intraoral cavity to enable teeth repair. The application mentions that the active component includes calcium phosphate powder and γ-PGA colloid to aid teeth repair. Nevertheless, it does not specifically mention the combination of γ-PGA and calcium phosphate and the effects that it may produce. US 20090042161 provides a device for retention at dental sites within the intraoral cavity to enable the prevention of dental caries. Nevertheless, it does not mention the combination of γ-PGA and calcium phosphate and the effects that it may produce.

US 20030124066, US 20030152525 and U.S. Pat. No. 6,863,882 all provide an oral care composition, such as toothpaste. They mention that the composition includes a phosphopeptide-amorphous calcium phosphate complex and a calcium chelator for use in improving fluoride stability. Nevertheless, it does not specifically mention the combination of γ-PGA and calcium phosphate and the effects that it may produce. US 20080171001 also provides toothpaste including a phosphopeptide-amorphous calcium phosphate complex to enable the mineralization of teeth. Nevertheless, it does not mention the combination of γ-PGA and calcium phosphate and the effects that it may produce.

U.S. Pat. Nos. 5,837,674 and 6,306,822 are related to phosphopeptides used to reduce bone loss or weakening. U.S. Patent Publication Nos. 20060204580, 20040131562, 20030232071, 20060204581, 20050152990, and U.S. Pat. No. 7,455,854 are all related to a biomimetic of bone or a biomimetic hard tissue. US 20090035355 is related to agglomerates comprising calcium-hydrocolloid-composite materials to promote repair of tooth material. Nevertheless, they do not mention the combination of γ-PGA and calcium phosphate and the effects that it may produce.

SUMMARY OF THE INVENTION

An aim of the invention is to provide a calcium phosphate complex and a composition containing the same which are able to buffer oral acidity and prevent caries effect.

It is another aim of the invention to provide a calcium phosphate complex and a composition containing the same which can stabilize amorphous calcium phosphate (ACP), maintain its ability to dissolve and at the same time repair teeth by releasing an appropriate ratio of calcium and phosphate ions.

It is another aim of the invention to provide a calcium phosphate complex and a composition containing the same, which can increase the duration of its retention in the mouth.

It is another aim of the invention to provide a calcium phosphate complex and a composition containing the same, which can increase dental surface hardness, facilitate closure of dentinal tubules and alleviate dental caries.

It is another aim of the invention to provide a calcium phosphate complex and a composition containing the same, which can avoid adverse effects caused by milk protein allergy.

The present invention provides an oral care composition comprising a calcium phosphate complex in which γ-polyglutamic acid (γ-PGA) is chelated with an amorphous calcium phosphate (ACP). Preferably, γ-PGA and ACP is in a ratio of from 1%:99% to 99%:1%. More preferably, the ratio range is from 10% to 90%:90% to 10%, 10% to 80%:90% to 20%, 20% to 80%:80% to 20%, or 30% to 70%:70% to 30%.

The present invention further provides a process for preparing a calcium phosphate complex, comprising: formulating a γ-polyglutamic acid solution, preparing a calcium containing solution and a phosphate containing solution separately and adding them into the γ-polyglutamic acid solution, stirring the calcium and phosphate containing γ-polyglutamic acid solution to precipitate a γ-PGA-ACP complex, and drying the precipitated complex.

DETAILED DESCRIPTION OF THE INVENTION

An "oral surface" herein encompasses any soft or hard surface within the mouth, including surfaces of the tongue, hard and soft palate, buccal mucosa, periodontal, gingival and dental surface. A "dental surface" herein is a surface of a natural tooth or a hard surface of artificial dentition including a crown, cap, filling, bridge, denture, dental implant and the like.

An oral composition of the present invention can take any form suitable for application to an oral surface. In various illustrative embodiments, the composition can be a liquid solution suitable for irrigating, rinsing or spraying; a dentifrice such as a powder, toothpaste or dental gel; a polishing abrasive such as a powder or gel; a periodontal gel; a liquid suitable for painting a dental surface (e.g., a liquid whitener); a chewing gel (e.g., chewing gum); a dissolvable, partially dissolvable or non-dissolvable film or strip (e.g., a whitening strip, a dental surface repair paste); a dentinal tubule sealer, a dental cream (e.g., a dental cleaning mousse); a dental filler; a dental floss; a food additive; an edible strip; and a buccal tablet, etc. The composition can contain active and/or carrier ingredients in addition to those recited above.

In certain embodiments, the composition is adapted for application to an oral surface of a small domestic animal; for example a cat or dog. Such a composition is typically edible or chewable by animals, and can take the form, for example, of a cat or dog food, processed product or toy.

In one embodiment, an oral composition is provided that contains a complex formed by chelating the γ-polyglutamic acid (γ-PGA) with an amorphous calcium phosphate (ACP). The ratio of γ-PGA to ACP can be 1% to 99%:99% to 1%, preferably 10% to 90%:90% to 10%, 10% to 80%:90% to 20%, 20% to 80%:80% to 20%, or 30% to 70%:70% to 30%.

In one embodiment, a process for preparing a calcium phosphate complex is provided, comprising the steps of: formulating a γ-polyglutamic acid solution, preparing a calcium containing solution and a phosphate containing solution separately and adding them to the γ-polyglutamic acid solution, stirring the calcium and phosphate containing γ-polyglutamic acid solution to precipitate a γ-PGA-ACP complex, and drying the precipitated complex.

The γ-PGA can be the acid form, the salt form or a mixture thereof. The γ-PGA salt can include a metal ion selected from the group consisting of univalent metal ions and bivalent metal ions. For example, the γ-PGA salt can comprise a salt selected from the group consisting of γ-polyglutamic sodium, γ-polyglutamic potassium, γ-polyglutamic calcium, γ-polyglutamic magnesium, and γ-polyglutamic zinc salt.

The calcium containing solution can comprise a calcium solution selected from the group consisting of calcium chloride, calcium hydroxide, and calcium nitrate solution.

The phosphate containing solution can comprise a solution (or salt or compound) selected from the group consisting of disodium hydrogen phosphate and dipotassium hydrogen phosphate solution (salt).

In one embodiment, an oral composition (e.g., a liquid solution for rinsing or spraying, a dentifrice, a toothpaste, a chewing gum, a dental floss, a buccal tablet, etc.) is provided, comprising, in addition to the γ-PGA-ACP complex described above, at least one oral acceptable antimicrobial (e.g., antibacterial) component, such as ursolic acid, carnosic acid, rosmarinic acid, carnosol, oleanolic acid or the mixture thereof, or selected from the group consisting of halogenated diphenylethers or the groups consisting of antibacterial phenolic compounds. One embodiment of the halogenated diphenylethers is triclosan. Examples of antibacterial phenolic compounds include 4-allylcatechol, p-hydroxybenzoic acid esters including benzylparaben, butylparaben, ethylparaben, methylparaben and propylparaben, 2-benzylphenol, butylated hydroxyanisole, butylated hydroxytoluene, capsaicin, carvacrol, creosol, eugenol, guaiacol, halogenated bisphenolics including hexachlorophene and bromochlorophene, 4-hexyl-resorcinol, 8-hydroxyquinoline and salts thereof, salicylic acid esters including menthyl salicylate, methyl salicylate and phenyl salicylate, phenol, pyrocatechol, salicylanilide, thymol, triclosan and triclosan monophosphate.

The phenolic compound is optionally present in a total amount of about 0.01% to about 10% by weight. For example, the total concentration of the phenolic compound in a toothpaste or gel dentifrice or mouth rinse of the present invention can be about 0.01% to about 5%, for example about 0.1% to about 2%, about 0.2% to about 1% or about 0.25% to about 0.5%.

Other suitable antibacterial agents include, but are not limited to, copper (II) compounds such as copper (II) chloride, fluoride, sulfate and hydroxide, zinc ion sources such as zinc acetate, zinc citrate, zinc gluconate, zinc glycinate, zinc oxide, zinc sulfate and sodium zinc citrate, phthalic acid and salts thereof such as magnesium monopotassium phthalate, hexetidine, octenidine, sanguinarine, benzalkonium chloride, domiphen bromide, alkylpyridinium chlorides such as cetylpyridinium chloride (CPC) (including combinations of CPC with zinc and/or enzymes), tetradecylpyridinium chloride and N-tetradecyl-4-ethylpyridinium chloride, iodine, sulonamides, bisbiguanides such as alexidine, chlorhexidine and chlorhexidine digluconate, piperidino derivatives such as delmopinol and octapinol, magnolia extract, grapeseed extract, menthol, geraniol, citral, eucalyptol, antibiotics such as augmentin, amoxicillin, tetracycline, doxycycline, minocycline, metranidazole, neomycin, kanamycin and clindamycin, and the like. One or more of the above described antimicrobial agents are optionally present in an antimicrobial effective total amount, typically about 0.05% to about 10%, for example about 0.1% to about 3% by weight, of the composition.

In one embodiment, an oral composition (e.g., a dentifrice, a toothpaste) is provided, optionally comprising, in addition to the γ-PGA-ACP complex described above, optionally, a wetting agent and at least one polishing material.

In one embodiment, an oral composition (e.g., a liquid solution for rinsing or spraying, a dentifrice, a toothpaste, a chewing gum, a dental floss, a buccal tablet, etc.) is provided, optionally comprising, in addition to the γ-PGA-ACP complex described above, other ingredients including but not limited to anticalculus agents, tartar control agents, anionic carboxylate polymers, viscosity modifiers, surfactants, breath freshening agents, flavorants, and the like. The ingredients mentioned above can be combined for the desired property or application.

Suitable anticalculus agents include, but are not limited to, phosphates and polyphosphates (for example pyrophosphates), polyaminopropanesulfonic acid (AMPS), zinc citrate trihydrate, polypeptides such as polyaspartic and γ-polyglutamic acids, polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts. Useful inorganic phosphate and polyphosphate salts include, for example, monobasic, dibasic and tribasic sodium phosphates, sodium tripolyphosphate, tetrapolyphosphate, mono-, di-, tri- and tetras odium pyrophosphates, disodium dihydrogen pyrophosphate, sodium trimetaphosphate, sodium hexametaphosphate and the like, wherein sodium can optionally be replaced by potassium or ammonium. Other useful anticalculus agents include anionic polycarboxylate polymers. The anionic polycarboxylate polymers contain carboxyl groups on a carbon backbone and include polymers or copolymers of acrylic acid, methacrylic, and maleic anhydride, and polyvinyl methyl ether/maleic anhydride (PVME/MA) copolymers. Other useful anticalculus agents include sequestering agents including hydroxycarboxylic acids such as citric, fumaric, malic, glutaric and oxalic acids such as ethylenediaminetetraacetic acid (EDTA). One or more anticalculus agents are optionally present in the composition in an anticaculus effective total amount, typically about 0.01% to about 50%, for example about 0.05% to about 25% or about 0.1% to about 15% by weight.

In one embodiment, an oral composition (e.g., a liquid solution for rinsing or spraying, a dentifrice, a toothpaste, a chewing gum, a dental floss, a buccal tablet, etc.) is provided, optionally comprising, in addition to the γ-PGA-ACP complex described above, an oral acceptable stannous ion source useful, for example, in helping reduce gingivitis, plaque, calculus, or caries. Suitable stannous ion sources include but are not limited to stannous fluoride, other stannous halides such as stannous chloride dehydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally present in a total amount of about 0.01% to about 10%, for example about 0.1% to about 7% or about 1% to about 5% by weight of the composition.

In one embodiment, an oral composition (e.g., a liquid solution for rinsing or spraying, a dentifrice, a toothpaste, a chewing gum, a dental floss, a buccal tablet, etc.) is provided, optionally comprising, in addition to the γ-PGA-ACP complex described above, an oral acceptable zinc ion source useful, for example, as an antimicrobial, anticalculus or breath freshening agent. Suitable zinc ion sources include but are not limited to, zinc acetate, zinc citrate, zinc gluconate, zinc glycinate, zinc oxide, zinc sulfate, sodium zinc citrate and the like. One or more zinc ion sources are optionally present in a total amount of about 0.05% to about 3%, for example about 0.1% to about 1%, by weight of the composition.

In one embodiment, an oral composition (e.g., a liquid solution for rinsing or spraying, a dentifrice, a toothpaste, a chewing gum, a dental floss, a buccal tablet, etc.) is provided, optionally comprising, in addition to the γ-PGA-ACP complex described above, an oral acceptable breath freshening agent. One or more such agents can be present in a breath freshening effective total amount. Suitable breath freshening agents include but are not limited to, zinc salts such as zinc gluconate, zinc citrate and zinc chlorite, α-ionone and the like.

In one embodiment, an oral composition (e.g., a liquid solution for rinsing or spraying, a dentifrice, a toothpaste, a chewing gum, a dental floss, a buccal tablet, etc.) is provided, comprising, in addition to the γ-PGA-ACP complex described above, optionally at least one oral acceptable antiplaque, including plaque disrupting agent. One or more such agents can be present in an antiplaque effective total amount. Suitable antiplaque agents include but are not limited to, stannous, copper, magnesium and strontium salts, dimethicone copolyol, papain, glucoamylase, glucose oxidase, urea, calcium lactate, calcium glycerophosphate, strontium polyacrylates and chelating agents such as citric and tartaric acids and alkali metal salts thereof.

In one embodiment, an oral composition (e.g., a liquid solution for rinsing or spraying, a toothpaste, a dental gel) is provided, comprising, in addition to the γ-PGA-ACP complex described above, optionally at least one oral acceptable anti-inflammatory agent. One or more such agents are present in an anti-inflammatory effective total amount. Suitable anti-inflammatory agents include but are not limited to, steroidal agents such as flucinolone and hydrocortisone, and nonsteroidal agents (NSAIDs) such as ketorolac, flurbiprofen, ibuprofen, naproxen, indomethacin, diclofenac, etodolac, sulindac, tolmetin, ketoprofen, fenoprofen, piroxicam, nabumetone, aspirin, diflunisal, meclofenamate, mefenamic acid, oxyphenbutazone and phenylbutazone.

In one embodiment, an oral composition (e.g., a liquid solution for rinsing or spraying, a dentifrice, a toothpaste, a chewing gum, a dental floss, a buccal tablet, etc.) is provided, comprising, in addition to the γ-PGA-ACP complex described above, optionally at least one oral acceptable fluoride ion sources useful as anticaries agent. Suitable fluoride ion sources include fluoride, monofluorrophosphate and fluorosilicate salts and amine fluorides, including olaflur (N'-octadecyltrimethylendiamine-N,N,N'-tris(2-ethanol)-dihydrofluoride).

One or more fluoride-releasing salts are optionally present in an amount providing a total of about 100 to about 20,000 ppm, about 200 to about 5,000 ppm, or about 500 to about 2,500 ppm, fluoride ions. Where the fluoride-releasing salt used is sodium fluoride, an amount of about 0.01% to about 5%, about 0.05% to about 1% or about 0.1% to about 0.5% by weight can be present in the composition.

In one embodiment, an oral composition (e.g., a liquid solution for rinsing or spraying, a dentifrice, a toothpaste, a chewing gum, a dental floss, a buccal tablet, etc.) is provided, optionally comprising, in addition to the γ-PGA-ACP complex described above, other ingredients such as enzymes, vitamins and anti-adhesion agents. Enzymes such as proteases can be added for anti-stain and other effects. Examples of vitamins include vitamin C, vitamin E, vitamin B5, and folic acid. Anti-adhesion agents include solbrol and ficin.

Useful carriers for optional inclusion in a composition of the invention are diluents, abrasives, bicarbonate salts, pH modifying agents, surfactants, foam modulators, thickening agents, viscosity modifiers, humectants, sweeteners, flavorants and colorants. One or more carriers can be optionally present. Carriers should be selected for compatibility with each other and with other ingredients of the composition.

In one embodiment, the preferred diluent is water and in some compositions such as mouthwash and whitening liquids is commonly accompanied by an alcohol, e.g., ethanol. The weight ratio of water to alcohol in a mouthwash composition is generally about 1:1 to about 20:1, for example about 3:1 to about 20:1 or about 4:1 to about 10:1. In a whitening liquid, the weight ratio of water to alcohol can be within or below the above ranges, for example about 1:10 to about 2:1.

The abrasive can be, for example, a polishing agent that is useful as a brightener. Any orally acceptable abrasive can be used, but type, fineness (particle size and amount of abrasive should be selected so that tooth enamel is not excessively abraded in normal use of the composition. Suitable abrasives include but are not limited to silica, alumina, insoluble phosphates, calcium carbonate, resinous abrasives such as urea-formaldehyde condensation products and the like. Insoluble phosphates useful as abrasives are orthophosphates, polymetaphosphates and pyrophosphates. Illustrative examples are dicalcium orthophosphate dehydrate, calcium pyrophosphate, β-calcium pyrophosphate, tricalcium phosphate, calcium polymetaphosphate and insoluble sodium polumetaphosphate. One or more abrasives are optionally present in an abrasive effective total amount, typically about 5% to about 90%, for example about 10% to about 50% or about 15% to about 30% by weight of the composition. Average particle size of an abrasive, if present, is generally about 0.1 to about 30 μm, for example about 0.5 to about 10 μm.

Bicarbonate salt can be utilized to impart a clean feel to teeth due to effervescence and release of carbon dioxide. Any orally acceptable bicarbonate can be used, including but not limited to alkali metal bicarbonates such as sodium and potassium bicarbonates, ammonium bicarbonate and the like. One or more bicarbonate salts are optionally present in a total amount of 0.1% to about 50%, for example about 1% to about 20% by weight of the composition.

A pH modifying agent includes acidifying agents to lower pH, basifying agents to raise pH and buffering agents to control pH within a desired range. For example, one or more compounds selected from acidifying, basifying and buffering agents can be included to provide a pH of about 2 to about 10, or in various illustrative embodiments about 2 to about 8, about 3 to about 9, about 4 to about 8, about 5 to about 7, about 6 to about 10, about 7 to about 9, etc. Any orally acceptable pH modifying agent can be used, including but not limited to carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, borates, silicates, phosphates (e.g., monosodium phosphate, trisodium phosphate, pyrophosphate salts, etc.), imidazole and the like. One or more pH modifying agents are optionally present in a total amount effective in maintaining the composition in an orally acceptable pH range.

Surfactants can be used, for example, to compatibilize other components of the composition and thereby provide enhanced stability, to help in cleaning the dental surface through detergency, and to provide foam upon agitation, e.g., during brushing with a dentifrice composition of the invention. Any orally acceptable surfactant, most of which are anionic, nonionic or amphoteric, can be used. Suitable anionic surfactants include but are not limited to water-soluble salts of $C_{8-20}$alkyl sulfates, sulfonated monoglycerides of $C_{8-20}$fatty acids, sarcosinates, taurates and the like. Illustrative examples of these and other classes include sodium lauryl sulfate, sodium coconut monoglyceride sulfonate, sodium lauryl sarcosinate, sodium lauryl isoethionate, sodium laureth carboxylate and sodium dodecyl benzenesulfonate. Suitable nonionic surfactants include but are not limited to poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include but are not limited to derivatives of $C_{8-20}$aliphatic secondary and tertiary amines having an anionic group such as carboxylate, sulfate, sulfonate, phosphate or phosphonate. A suitable example includes cocoamidopropyl betaine. One or more surfactants are optionally present in a total amount of about 0.01% to about 10%, for example about 0.05% to about 5% or about 0.1% to about 0.2% by weight of the composition.

Foam modulators can be used to increase the amount, thickness or stability of foam generated by the composition upon agitation. Any orally acceptable foam modulator can be used, including but not limited to polyethylene glycols (PEGs) and polyoxyethylenes. High molecular weight PEGs are suitable, including those having an average molecular weight of about 200,000 to about 7,000,000 for example about 500,000 to about 5,000,000 or about 1,000,000 to about 2,500,000. One or more PEGs are optionally present in a total amount of about 0.1% to about 10%, for example about 0.2% to about 5% or about 0.25% to about 2% by weight of the composition.

Thickening agents are used, for example, to impart a desired consistency and/or mouth feel to the composition. Any orally acceptable thickening agent can be used, including but not limited to carbomers, also known as carboxyvinyl polymers, carrageenans, also known as Irish moss and more particularly L-carrageenan (τ-carrageenan), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, colloidal silica and the like. One or more thickening agents are optionally present in a total amount of about 0.01% to about 15%, for example about 0.1% to about 10% or about 0.2% to about 5% by weight of the composition.

Viscosity modifier is used, for example, to inhibit settling or separation of ingredients or to promote redispersibility upon agitation of a liquid composition. Any orally acceptable viscosity modifier can be used, including but not limited to mineral oil, petrolatum, clays and organomodified clays, silica and the like. One or more viscosity modifiers are optionally present in a total amount of about 0.01% to about 10%, for example about 0.1% to about 5% by weight of the composition.

Wetting agents are used, for example, to prevent hardening of a tooth paste upon exposure to air. Any orally acceptable wetting agent can be used, including but not limited to polyhydric alcohols such as glycerin, sorbitol, xylitol or low molecular weight PEGs. Most wetting agents also function as sweeteners. One or more wetting agents are optionally present in a total amount of about 1% to about 70%, for example about 1% to about 50%, about 2% to about 25%, or about 5% to about 15% by weight of the composition.

Sweeteners can be used to enhance taste of the composition. Any orally acceptable natural or artificial sweetener can be used, including but not limited to dextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, dipeptide-based intense sweeteners, cyclamates and the like. One or more sweeteners are optionally present in a total amount depending strongly on the particular sweetener(s) selected, but typically about 0.005% to about 5% by weight of the composition.

Flavorants can be used to enhance the taste of the composition. Any orally acceptable natural or synthetic flavorant can be used, including but not limited to, vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants and the like. Also encompassed within flavorants herein are ingredients that provide fragrance and/or other sensory effect in the mouth, including cooling or warming effects. Such ingredients illustratively include menthol, menthyl acetate, menthyl lactate, camphor, eucalyptus oil, eucalyptol, anethole, eugenol, cassia, oxanone, α-irisone, propenyl guaiethol, thymol, linalool, benzaldehyde, cinnamaldehyde, N-ethyl-p-menthan-3-carboxamine, N,2,3-trimethyl-2-iso-propylbutanamide, 3-(1-menthoxy)-propane-1,2-diol, cinnamaldehyde glycerol acetal (CGA), menthone glycerol acetal (MGA) and the like. One or more flavorants are optionally present in a total amount of about 0.01% to about 5%, for example 0.1% to about 2.5% by weight of the composition.

Colorants include pigments, dyes, lakes and agents such as pearling agents imparting a particular luster or reflectivity. A colorant can serve a number of functions, including for example to provide a white or light-colored coating on a dental surface, to act as an indicator of locations on a dental surface that have been effectively contacted by the composition, and/or to modify appearance, in particular, color and/or opacity, of the composition to enhance attractiveness to the consumer. Any orally acceptable colorant can be used, including but not limited to talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride and the like. One or more colorants are optionally present in a total amount of about 0.001% to about 20%, for example about 0.01% to about 10% or about 0.1 to about 5% by weight of the composition.

In one embodiment, mouthwash and mouth rinse compositions are provided that contain water, one or more organic hydric compounds, and a γ-PGA-ACP complex of the invention described above, wherein the ratio of γ-PGA to ACP in the complex is 1% to 99%:99% to 1%, preferably 10% to 90%:90% to 10%, 10% to 80%:90% to 20%, 20% to 80%:80% to 20% or 30% to 70%:70% to 30%. The mouthwash and mouth rinse compositions are present in a total amount of about 1% to 10% by weight of the composition.

In one preferred embodiment, the composition includes the γ-PGA-ACP complex in an amount of about 1% to 5% or about 3% to about 5% by weight of the composition.

Flavorants such as those described above can be used. The one or more organic hydric compounds are orally acceptable organic solvents such as, without limitation, ethanol and glycerol. Optionally, the mouthwash and mouth rinse compositions contain a surfactant to aid in dispersal of the flavorants and antibacterial compositions.

In one embodiment, a chewing gum composition (e.g., chewing gum) is provided, comprising a gum base and a γ-PGA-ACP complex such as that described above, wherein the ratio of γ-PGA to ACP in the complex is 1% to 99%:99% to 1%, preferably 10% to 90%:90% to 10%, 10% to 80%:90% to 20%, 20% to 80%:80% to 20% or 30% to 70%:70% to 30%. In a preferred embodiment, the composition contains 1% to 10% of the complex by weight. Chewing gum composition typically contains at least one sweetening agent and at least one flavoring agent.

Gum base materials are known in the art and include natural or synthetic gum bases or mixtures thereof. Representative natural gums or elastomers include chicle, natural rubber, jelutong, balata, gutta-percha, lechi caspi, sorva, guttakay, crown gum, and perillo. Synthetic gums or elastomers include butadiene-styrene copolymers, polyisobutylene and isobutylene-isoprene copolymers. The gum base is incorporated in the chewing gum product at a concentration of about 10% to about 40% and preferably about 20% to about 35%. Sweetening agent and flavoring agent as described above can be used.

In one embodiment, an edible oral strip (e.g., chewing gum) is provided, comprising one or more polymeric film forming agents and a γ-PGA-ACP complex such as that described above, wherein the ratio of γ-PGA to ACP in the complex is 1% to 99%:99% to 1%, preferably 10% to 90%:90% to 10%, 10% to 80%:90% to 20%, 20% to 80%:80% to 20% or 30% to 70%:70% to 30%. In a preferred embodiment, the composition comprises the complex in an amount of about 1% to about 10% by weight. One or more polymeric film forming agents are selected from the group consisting of orally acceptable polymers such as pullulan, cellulose derivatives, and other soluble polymers, including those well-known in the art.

In one embodiment, toothpaste or gel composition is provided, comprising at least one wetting agent, a silica based abrasive compound (e.g., silica), optional anticalculus agents, and a γ-PGA-ACP complex such as that described above, wherein the ratio of γ-PGA to ACP in the complex is 1% to 99%:99% to 1%, preferably 10% to 90%:90% to 10%, 10% to 80%:90% to 20%, 20% to 80%:80% to 20% or 30% to 70%:70% to 30%. In a preferred embodiment, the composition comprises the complex in an amount of about 1% to about 15% by weight. Wetting agents and anticalculus as described above can be used. The toothpaste or gel composition can optionally contain other anticaries agents such as sodium fluoride, stannous fluoride, mono fluorophosphates, and the like. In addition to the wetting agent, the toothpaste or gel composition can contain about 1% to about 40% water by weight.

In one embodiment, an abrasive is provided, comprising a silica based abrasive compound (e.g., silica) and a γ-PGA-ACP complex such as that described above, wherein the ratio of γ-PGA to ACP in the complex is 1% to 99%:99% to 1%, preferably 10% to 90%:90% to 10%, 10% to 80%:90% to 20%, 20% to 80%:80% to 20% or 30% to 70%:70% to 30%. In a preferred embodiment, the composition comprises the complex in an amount of about 3% to about 20% by weight.

The components as described in the above embodiments can be combined in order to obtain the desired property or to conform to certain applications. All the embodiments are only illustrative without implying any restriction to the scope of the invention.

In the subject invention, γ-PGA chelates with ACP to form a core-shell structure. Since γ-PGA is highly absorbent, lubricous, acidity buffered, and electron negative in structure, it can be easily chelated with metal ions and thereby stabilize the amorphous structure of the ACP, and help to maintain its dissoluble property and facilitate its attachment to the oral surface, particular dental surfaces. ACP is a salt of calcium phosphate in which the ratio of calcium to phosphate is 1.5, and therefore can buffer acidity. By releasing calcium and phosphate ions, ACP aids in the treatment of dental caries. Therefore, the invention not only buffers acidity in the mouth and prevents caries, but can further promote repair of teeth and alleviate dental caries.

The examples below show that the composition containing the γ-PGA-ACP complex has improved acidity buffering and calcium release effects when compared to compositions without such complex.

The present invention is further defined in the following example(s). It should be understood that the example(s), while indicating preferred embodiments of the inventions, are given by way of illustration only. From the above discussion and the example(s), one skilled in the art can ascertain the essential characteristics of this invention and, without departing from the spirit and scope thereof, can make various changes and modifications to the invention to adapt it to various uses and conditions.

EXAMPLES

Example 1

Preparation of Calcium Phosphate Complex by Chelating the γ-Polyglutamic Acid (γ-PGA) with an Amorphous Calcium Phosphate (ACP)

Calcium chloride solution (1.5M, 25 ml) and disodium hydrogen phosphate (1M, 25 ml) were simultaneously added to the solution system containing 5 wt % of calcium form γ-PGA (50 ml) and mixed and stirred to precipitate the γ-PGA-ACP complex. The precipitated complex was dried and the calcium phosphate complex was obtained.

Figure 1:
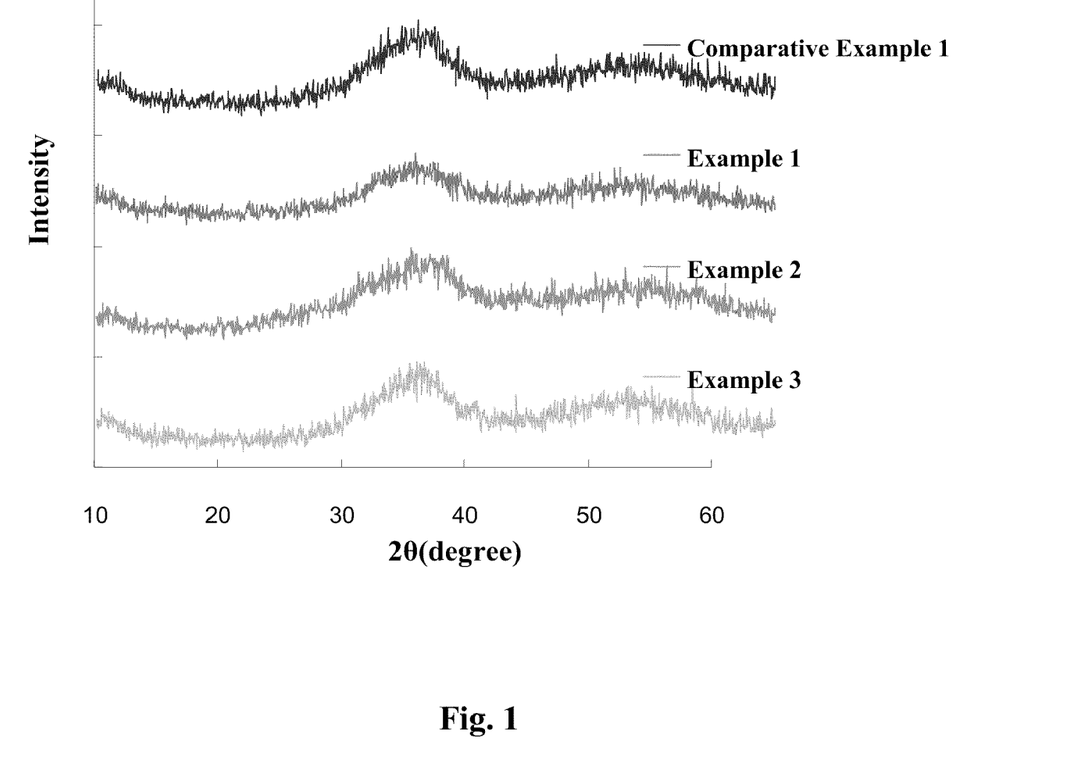
FIG. 1 shows the wide angle XRD results of the complex powders of Examples 1-3 and Comparative Example 1.

The obtained complex powder was analyzed by wide angle X-Ray diffractometer. The result is shown in FIG. 1. The complex of the invention is evidenced as an amorphous powder. As for the process, the complex of the invention can maintain its amorphous property without addition of an alkaline and thereby rendering the process easier, more convenient, and cost efficient.

Example 2

Preparation of Calcium Phosphate Complex by Chelating the γ-Polyglutamic Acid (γ-PGA) with an Amorphous Calcium Phosphate (ACP)

Calcium form γ-PGA solution (25 ml, 5 wt %) and disodium hydrogen phosphate (1M, 25 ml) were stirred for mixing to precipitate the γ-PGA-ACP complex. The precipitated complex was dried and the calcium phosphate complex was obtained.

The obtained complex powder was analyzed by the process described in Example 1. The result is shown in FIG. 1 and the effects are similar to Example 1.

Example 3

Preparation of Calcium Phosphate Complex by Chelating the γ-Polyglutamic Acid (γ-PGA) with an Amorphous Calcium Phosphate (ACP)

Calcium chloride solution (1.5M, 25 ml) and disodium hydrogen phosphate (1M, 25 ml) were directly mixed in water. The system controlled the pH value at 9 with sodium hydroxide. The solution as prepared above was added to the solution system containing 5 wt % of calcium form γ-PGA (50 ml) and mixed and stirred to precipitate the γ-PGA-ACP complex. The precipitated complex was dried and the calcium phosphate complex was obtained.

The obtained complex powder was analyzed by the process described in Example 1. The result is shown in FIG. 1 and the effects are similar to Example 1.

Comparative Example 1

Typical Process for Preparing an Amorphous Calcium Phosphate (ACP)

Calcium chloride solution (1.5M, 25 ml) and disodium hydrogen phosphate solution (1M, 25 ml) were mixed with water. The resulting solution was stirred for mixing while simultaneously being titrated with sodium hydroxide solution to maintain the pH value of 9 to 10, thereby the ACP complex is precipitated. The precipitated powder was dried and ACP was obtained.

The obtained complex powder was analyzed by the process described in Example 1. The result is shown in FIG. 1. The typical synthesis process of ACP requires alkaline to maintain the pH value and therefore is not cost efficient.

Example 4

Amorphous Property Stability Test

Figure 2:
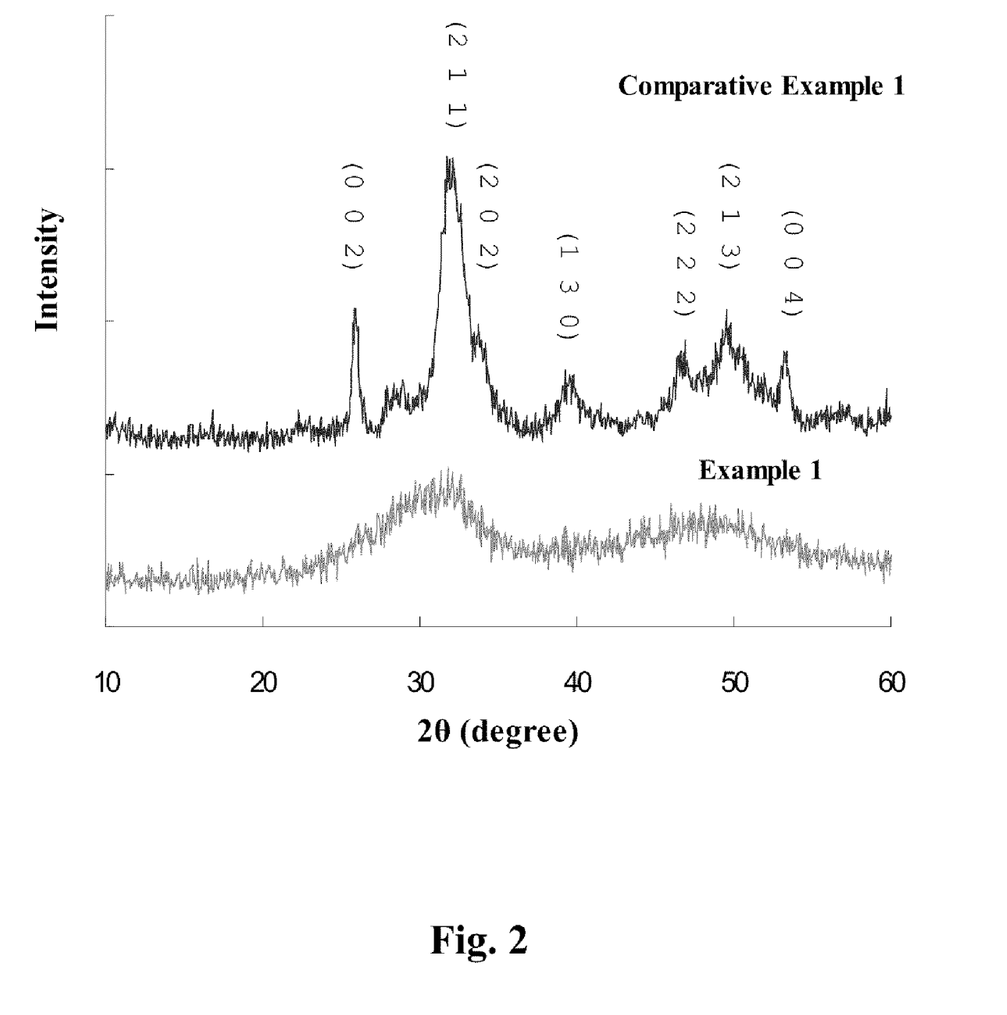
FIG. 2 shows the wide angle XRD results of the complex powders of the invention and the amorphous calcium phosphate after they were soaked in water for a period of time.

The calcium phosphate complex of the invention (Example 1) and ACP (Comparative Example 1) were separately placed in water, having a concentration of 5 wt %. Powders were retrieved after they were in the water for 48 hours and analyzed with a wide angle X-Ray diffractometer to test the ability of the powders to maintain the amorphous state. The results are shown in FIG. 2. The complex powder of the invention can maintain its amorphous state in water. On the other hand, the powders of Comparative Example 1, which do not have γ-PGA, transformed into crystal type calcium phosphate, which decreased the dissolution of the calcium and the phosphate ions due to the increase in crystallinity. The results further evidence that γ-PGA has the effect of stabilizing the ACP and thereby can stabilize the release of calcium and phosphate ions to promote repair of teeth.

Example 5

Comparison of Buffering Capacity

A calcium phosphate complex of the invention (Example 1), ACP (Comparative Example 1), and a casein phosphopeptide-amorphous calcium phosphate (CPP-ACP) based formulation, GC TOOTH MOUSSE™ (GC Corporation, Tokyo, Japan) were separately added into water at 10% in weight, and water was used as control group. The solutions were titrated with 1N HCl acid solution to obtain the variation of the pH value as a demonstration of the buffering property of the invention and the compared example.

Figure 3:
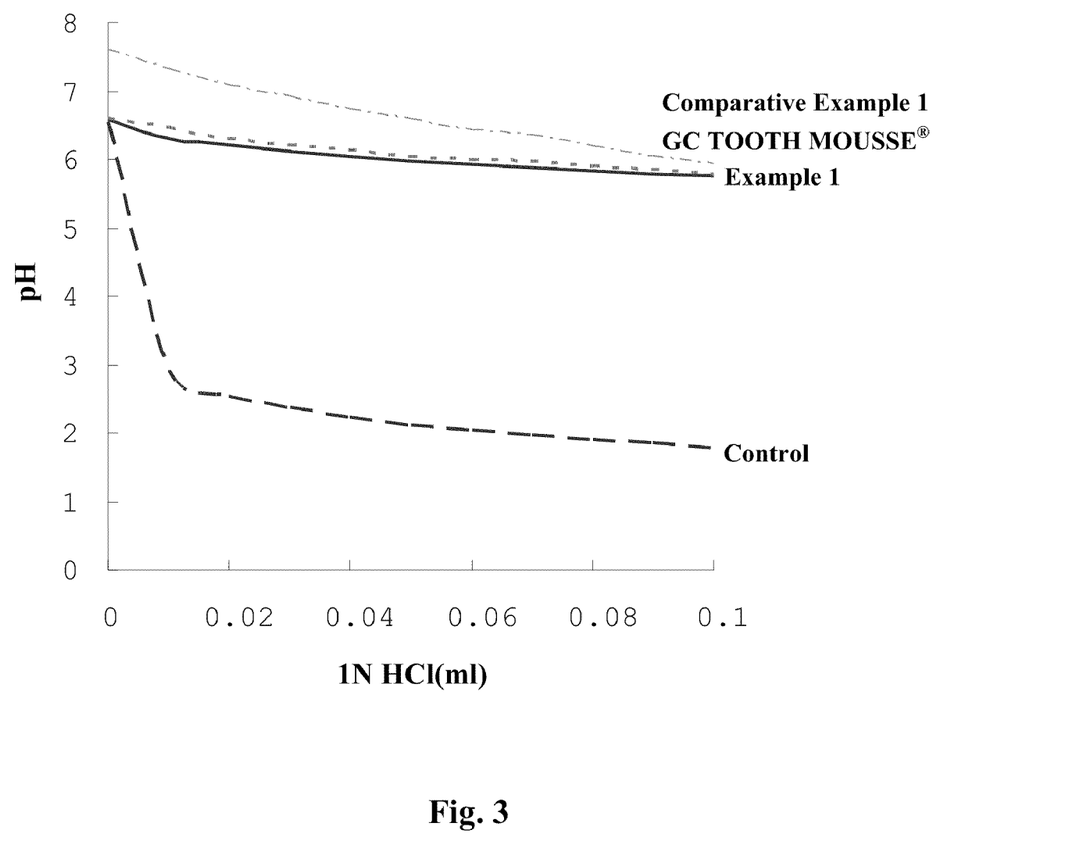
FIG. 3 shows the pH variation of titration of the complex of the invention, the amorphous calcium phosphate, and the CPP-ACP powder based composition.

As shown in FIG. 3, pH value dropped rapidly when HCl was titrated into water and the water became acidic. ACP has a buffering effect in water. Nevertheless, ACP transforms to crystalline calcium phosphate in water, resulting in poor solubility and compromising its buffering effect and effectiveness in comparison with the invention. The buffering effect of CPP-ACP, on the other hand, is comparable to that of the invention. Since the complex of the invention has an effective buffering property, it may help prevent caries resulting from acidic substances in the mouth, thereby protecting the teeth. In addition, since the invention does not utilize casein phosphopeptide, it can be used by people with milk protein allergy, unlike CPP-ACP.

Example 6

Comparison of Calcium Amount on the Oral Surface

A calcium phosphate complex of the invention (Example 1) and a casein phosphopeptide-amorphous calcium phosphate (CPP-ACP) based formulation, GC TOOTH MOUSSE™ (GC Corporation, Tokyo, Japan), were each separately prepared as a solution with 3% by weight. Water was used as control group. Three subjects washed their mouths with 30 ml of the solution three times a day for 30 seconds each time over a three-day period. There was no brushing of teeth, or use of other oral care products. Three days later, a dentist scraped the surface of the tissues with periodontal disease and teeth with periodontal curette to obtain the plaque and analyze the quantity of calcium. A 14-day break was taken between the two experiments to isolate and compare the effects of the different materials.

Figure 4:
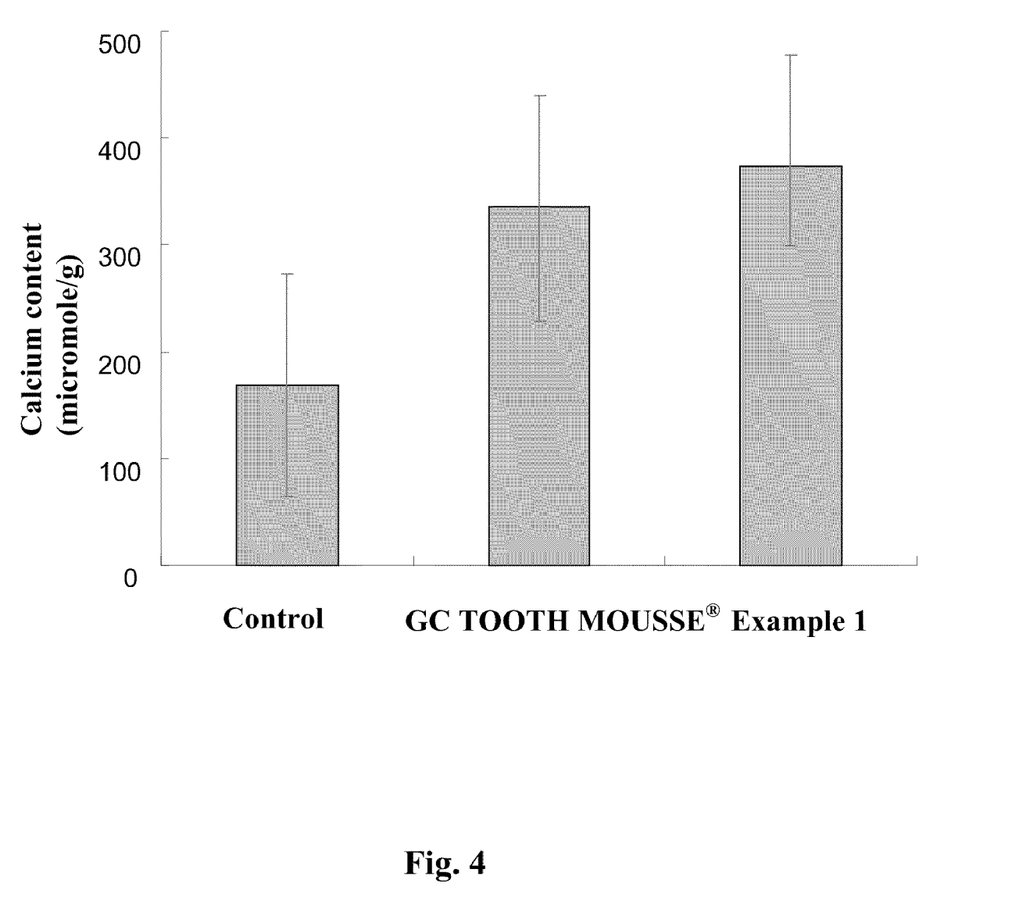
FIG. 4 shows a comparison of the amounts of the calcium attached between water, the complex of the invention, and the CPP-ACP powder based composition.

The results are shown in FIG. 4. It is found that for water, least calcium was adhered to the oral surface, representing that the calcium ions are those originally existing in saliva and that the calcium ions deposited on the plaque resulted from abstaining from brushing the teeth. For the CPP-ACP based GC TOOTH MOUSSE™ solution, calcium was increased by 89.8% in three days. But the composition containing the complex of the invention increased the amount of calcium by 121.7%, exhibiting better calcium adhesion. Therefore, use of the invention in oral care products can help repair of teeth due to superior calcium adhesion.

Example 7

Mouthwash Rinse

Formulation 1

| Components | Weight (%) |
| --- | --- |
| flavorant | 1 |
| γ-PGA-ACP | 3 |
| water | sufficient amount |
| Total | 100 |

Formulation 2

| Components | Weight (%) |
| --- | --- |
| alcolhol | 20 |
| flavorant | 1 |
| sodium fluoride | 0.05 |
| γ-PGA-ACP | 3 |
| water | sufficient amount |
| Total | 100 |

Example 8

Toothpaste

| Components | Weight (%) |
| --- | --- |
| sodium polyacrylate | 10 |
| glycerol | 20 |
| xylitol | 10 |
| sodium fluoride | 0.05 |
| flavorant | 1 |
| γ-PGA-ACP | 15 |
| water | sufficient amount |
| Total | 100 |

Example 9

Chewing Gum

| Components | Weight (%) |
| --- | --- |
| arabic gum | 40 |
| crystalline xylitol | 30 |
| glycerol | 0.5 |
| flavorant | 1 |
| γ-PGA-ACP | 3 |
| water | sufficient amount |
| Total | 100 |

Example 10

Abrasive

| Components | Weight (%) |
| --- | --- |
| pumice powder | 5 |
| glycerol | 10 |
| ethylcellulose | 5 |
| flavorant | 1 |
| γ-PGA-ACP | 15 |
| water | sufficient amount |
| Total | 100 |

Example 11

Dental Gel

| Components | Weight (%) |
| --- | --- |
| glycerol | 5 |
| ethylcellulose | 5 |
| flavorant | 1 |
| γ-PGA-ACP | 10 |
| water | sufficient amount |
| Total | 100 |

Example 12

Comparison of Teeth Hardness

A composition of the invention (Example 11), a casein phosphopeptide-amorphous calcium phosphate (CPP-ACP) based GC TOOTH MOUSSE™ (GC Corporation, Tokyo, Japan), and ACP (Comparative Example 1) were each separately prepared as a solution with 10% by weight. Water was used as a control group. Healthy adult teeth were embedded and polished to provide an enamel plane platform. 1M acetic acid was used to erode and damage the surface of the platform for three minutes, after which the following steps were taken: The test materials were painted on the surface of the platform and left for 15, 30, or 60 minutes. The materials were then removed from the surface with water and a micro-hardness tester measured hardness by pressing a probe against the surface.

Figure 5:
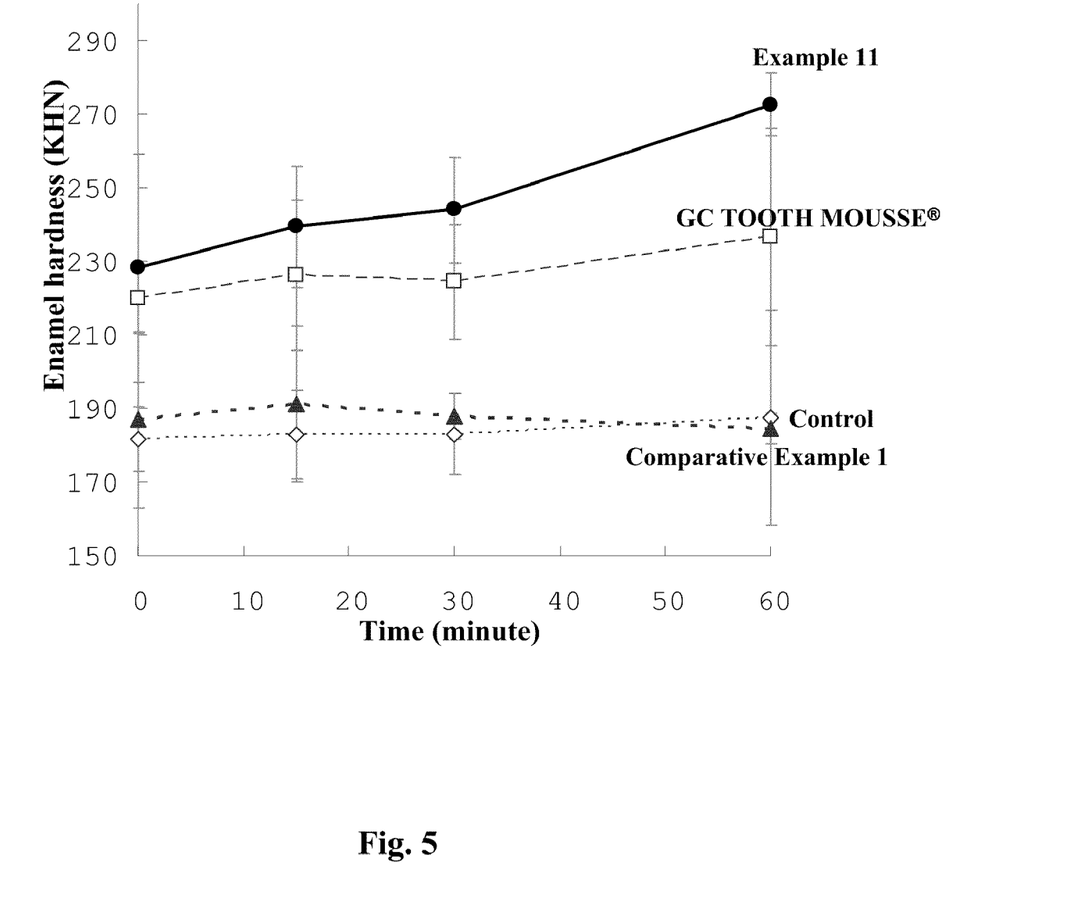
FIG. 5 shows the effects of the composition comprising the complex of the invention, the amorphous calcium phosphate, the CPP-ACP powder based composition, and water on the hardness of the enamel surface.

The results are shown in FIG. 5. It is found that water (control group) does not affect the hardness of the surface of the tooth or the condition of erosion. The solution containing ACP (Comparative Example 1) also does not affect the hardness of the surface, just like the control group. After 60 minutes, the GC TOOTH MOUSSE™ increased the hardness of the surface by 7.6%. In contrast, however, the complex of the invention increased the hardness of the surface by 19.4%, exhibiting superior hardening effect 2.5 times greater than GC TOOTH MOUSSE™. Therefore, use of the invention in oral care products can enhance the hardness of the dental surface, and thereby alleviate dental caries.

Example 13

Comparison of Closure of Dentinal Tubules

The complex of the invention can be useful in closing dentinal tubules. That is, it can reduce corrosion of dentinal tubules in caries, and prevent damage to the pulp chamber and resulting necrosis. The following experiment was designed to compare the dentinal tubule closing ability of a composition containing 15% by weight of the complex of the invention (Example 8), an Arginine-CaCO₃ based product, PRO-RELIEF™ (Colgate-Palmolive Corporation, New York, U.S.), and water (control group).

The teeth of healthy adult teeth were embedded and polished to prepare a dentinal tubule section. 1M acetic acid was used to clean the section for 15 seconds to ensure an opening of the dentinal tubule. Then, the following experiments were conducted: A dental slow-speed handler was mounted with a regular plastic head brush. An appropriate amount of sample was placed on the dentinal tubule section and the head brush was used to brush the surface of the section for 30 seconds. Deionized water was used for 10 seconds to clear it and then a lens wiper was used to absorb the water. The section was then put in the phosphate buffer for 10 minutes. After 28 repetitions, areas of $1.6 \times 10^4$ μm² in the section were taken and observed under microscope, and software analysis was conducted to measure the total area of the holes. A comparison was made for the samples. The same tests were conducted on samples in the phosphate buffer for six days, and the differences in degradation between samples were measured.

Figure 6:
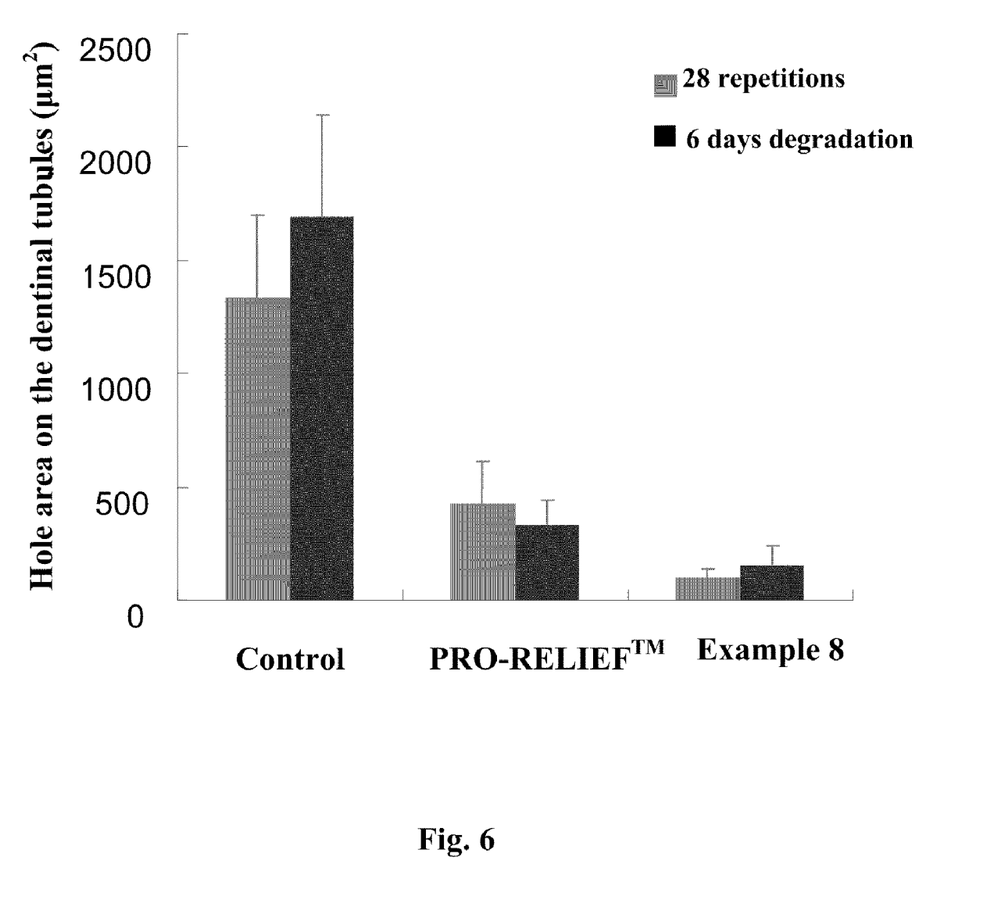
FIG. 6 shows the effects of the composition comprising the complex of the invention, the Arginine-CaCO$_3$ based composition, and water on closing of dentinal tubules.

The results are shown in FIG. 6. The control group has no effect on closing of the dentinal tubule. In contrast, the composition of Example 8 has an effect in closing the holes and achieves better results than PRO-RELIEF™. In addition, after six days of degradation in the phosphate buffer, Example 8 still demonstrates better results. The composition can stabilize and maintain the holes, thereby achieving better results in closing dentinal tubules and maintaining durability.

What is claimed is:

1. An oral composition, comprising a γ-polyglutamic acid (γ-PGA) calcium phosphate complex formed by chelating γ-polyglutamic acid (γ-PGA) with amorphous calcium phosphate (ACP), wherein the ratio of γ-PGA to ACP is about 5% to about 95%:about 95% to about 5%.

2. The oral composition according to claim 1, wherein the γ-PGA is the acid form, the salt form or the mixture thereof.

3. The oral composition according to claim 2, wherein the γ-PGA salt is selected from the group consisting of γ-polyglutamic sodium, γ-polyglutamic potassium, γ-polyglutamic calcium, γ-polyglutamic magnesium, and γ-polyglutamic zinc.

4. The oral composition according to claim 1, wherein the ratio of γ-PGA to ACP in the complex is 10% to 90%:90% to 10%, 10% to 80%:90% to 20%, 20% to 80%:80% to 20%, or 30% to 70%:70% to 30%.

5. The oral composition according to claim 1, wherein the complex formed by chelating γ-PGA with the ACP is in an amount of about 1% to about 25% by weight of the composition.

6. The oral composition according to claim 1, wherein the complex formed by chelating γ-PGA with the ACP is in an amount of about 2% to about 20% by weight of the composition.

7. The oral composition according to claim 1, wherein the complex formed by chelating γ-PGA with the ACP is in an amount of about 3% to about 15% by weight of the composition.

8. A process for preparing a calcium phosphate complex of claim 1, comprising the steps of: formulating a γ-PGA solution; adding a calcium containing solution and a phosphate containing solution to the γ-PGA solution, stirring the calcium and phosphate containing γ-PGA solution to precipitate a γ-PGA-ACP complex.

9. The process according to claim 8, wherein the calcium containing solution and the phosphate containing solution are mixed before being added to the γ-PGA solution.

10. The process according to claim 8, wherein the calcium containing solution and the phosphate containing solution are added to the γ-PGA solution simultaneously.

11. The process according to claim 8, wherein the calcium containing solution is added to the γ-PGA solution before the phosphate containing solution.

12. The process according to claim 8, wherein the γ-PGA solution comprises a metal ion selected from the group consisting of univalent metal ions and bivalent metal ions.

13. The process according to claim 8, wherein the γ-PGA solution comprises a γ-polyglutamic salt selected from the group consisting of γ-polyglutamic sodium, γ-polyglutamic potassium, γ-polyglutamic calcium, γ-polyglutamic magnesium, and γ-polyglutamic zinc salt.

14. The process according to claim 8, wherein the calcium containing solution comprises a calcium solution (or salt) selected from the group consisting of calcium chloride, calcium hydroxide, and calcium nitrate solution (or salt).

15. The process according to claim 8, wherein the phosphate containing solution is selected from the group consisting of disodium hydrogen phosphate solution and dipotassium hydrogen phosphate solution.

16. A method of using the oral composition as claimed in claim 1 for making a dentifrice, a toothpaste, a periodontal gel, a chewing gel, a whitening strip, a dental surface repair paste, a polishing abrasive, a dentinal tubule sealer, a dental cream, a food additive, a dental floss, an edible strip, a dental floss, a dental gel, or a buccal tablet.

17. A mouthwash rinse, comprising the oral composition as claimed in claim 1.

18. A toothpaste, comprising the oral composition as claimed in claim 1.

19. A chewing gum, comprising the oral composition as claimed in claim 1.

20. A polishing abrasive, comprising the oral composition as claimed in claim 1.

21. A dental gel, comprising the oral composition as claimed in claim 1.

22. An oral composition, comprising a γ-polyglutamic acid (γ-PGA) calcium phosphate complex formed by chelating γ-PGA with amorphous calcium phosphate (ACP) according to the steps of: (a) providing a γ-PGA solution; (b) adding a calcium containing solution and a phosphate containing solution to the γ-PGA solution; and (c) stirring the calcium and phosphate containing γ-PGA solution to precipitate a γ-PGA-ACP complex, wherein the ratio of γ-PGA to ACP is about 5% to about 95%:about 95% to about 5%.

* * * * *